US011198822B2

(12) United States Patent
Wang et al.

(10) Patent No.: US 11,198,822 B2
(45) Date of Patent: Dec. 14, 2021

(54) PROCESSES TO CONVERT NAPHTHA TO HEAVIER PRODUCTS

(71) Applicant: ExxonMobil Research and Engineering Company, Annandale, NJ (US)

(72) Inventors: Kun Wang, Bridgewater, NJ (US); Jonathan E. Mitchell, Easton, PA (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 25 days.

(21) Appl. No.: 16/833,804

(22) Filed: Mar. 30, 2020

(65) Prior Publication Data

US 2020/0325401 A1 Oct. 15, 2020

Related U.S. Application Data

(60) Provisional application No. 62/831,891, filed on Apr. 10, 2019.

(51) Int. Cl.
*C10G 11/05* (2006.01)
*C07C 2/00* (2006.01)
*C10G 11/10* (2006.01)

(52) U.S. Cl.
CPC .............. *C10G 11/05* (2013.01); *C07C 2/00* (2013.01); *C10G 11/10* (2013.01); *C10G 2300/1044* (2013.01); *C10G 2300/4006* (2013.01); *C10G 2300/4012* (2013.01); *C10G 2300/4018* (2013.01); *C10G 2300/4025* (2013.01); *C10G 2400/30* (2013.01)

(58) Field of Classification Search
None
See application file for complete search history.

(56) References Cited

U.S. PATENT DOCUMENTS

| | | | | |
|---|---|---|---|---|
| 3,304,340 A * | 2/1967 | Noll | ...... | C10G 47/00 585/256 |
| 3,879,486 A * | 4/1975 | Mitchell, Jr. | ...... | C07C 2/76 585/417 |
| 4,224,141 A * | 9/1980 | Morrison | ...... | B01J 29/40 208/134 |
| 4,283,584 A * | 8/1981 | Chester | ...... | B01J 29/40 208/66 |
| 4,720,602 A * | 1/1988 | Chu | ...... | C07C 2/00 585/407 |
| 4,804,801 A * | 2/1989 | Yan | ...... | B01J 29/48 585/407 |
| 4,891,463 A * | 1/1990 | Chu | ...... | C07C 5/41 585/415 |
| 5,414,184 A | 5/1995 | Wu et al. | | |
| 5,763,348 A * | 6/1998 | Fung | ...... | B01J 29/62 208/140 |
| 5,763,727 A | 6/1998 | Collins et al. | | |
| 5,827,422 A * | 10/1998 | Drake | ...... | B01J 29/40 208/135 |
| 6,566,569 B1 | 5/2003 | Chen et al. | | |
| 2001/0008949 A1* | 7/2001 | Wu | ...... | B01J 27/22 585/420 |
| 2012/0277503 A1* | 11/2012 | Wegerer | ...... | C10G 59/00 585/301 |
| 2017/0007992 A1* | 1/2017 | Lishchiner | ...... | B01J 37/04 |
| 2019/0336951 A1* | 11/2019 | Snell | ...... | B01J 29/084 |
| 2020/0087587 A1* | 3/2020 | D'Acosta | ...... | C10L 1/06 |

OTHER PUBLICATIONS

Schmidt, R.; Welch, M.B.; Anderson, R.L.; Sardashti, M.; Randolph, B.B. "Disproportionation of Light Paraffins", Energy and Fuels, 2008, 22, 1812-1823.
Burnett, R.L.; Hughes, T.R. "Mechanism and Poisoning of the Molecular Redistribution Reaction of Alkanes with a Dual-Functional Catalyst System", Journal of Catalysis, 1973, 31, 55-64.
U.S. Appl. No. 62/783,490.

* cited by examiner

*Primary Examiner* — Tam M Nguyen
(74) *Attorney, Agent, or Firm* — Robert A. Migliorini

(57) ABSTRACT

In an embodiment, a process for converting a hydrocarbon feed includes introducing a hydrocarbon feed comprising a $C_2$-$C_{50}$ acyclic alkane and a $C_3$-$C_{50}$ cyclic alkane to a catalyst composition in a reactor. The process further includes converting the hydrocarbon feed in the reactor under reactor conditions to a product mixture comprising at least one of a $C_6$-$C_9$ aromatic product or a $C_{12+}$ distillate product.

24 Claims, No Drawings

PROCESSES TO CONVERT NAPHTHA TO HEAVIER PRODUCTS

CROSS-REFERENCE TO RELATED APPLICATIONS

This application claims priority to U.S. Provisional Application No. 62/831,891 filed Apr. 10, 2019, which is herein incorporated by reference in its entirety.

FIELD

The present disclosure generally relates to processes to upgrade hydrocarbon feeds, and more particularly to low temperature, liquid phase conversion of naphtha to high octane gasoline and/or distillate products over an acid catalyst.

BACKGROUND

As the production of shale and tight oils is increasing in the United States, natural gas liquids (NGL) and naphtha are becoming increasingly abundant. NGL and naphtha contain a variety of hydrocarbons, such as ethane, light naphtha, and heavy naphtha, useful for downstream processing. Ethane to light naphtha range paraffins are largely fed to steam crackers or dehydrogenated to make olefins. For example, ethane may be steam-cracked to make ethylene (largely in the US), and light naphtha (having a boiling point of 60° F.-160° F., 15° C.-71° C.) may be steam cracked to make ethylene, propylene, and small volumes of dienes (practiced largely in Asia and Europe). Short-chain alkanes (e.g., propane and isobutane) may also be converted to their corresponding olefins using dehydrogenation technologies. In a refinery, light naphtha may be blended directly into gasoline; however, its low octane and relatively high vapor pressure typically limits it to 5% or less of the gasoline pool. To boost its octane, light naphtha may be sent to an isomerization unit before gasoline blending.

Heavy naphtha (having a boiling point of 160° F.-360° F., 70° C.-185° C.) is typically made of molecules having 6-9 carbon atoms (e.g., cyclohexane, heptane).

The low octane of heavy naphtha makes direct blending into gasoline undesirable, so heavy naphtha is typically fed to catalytic reformers in order to produce aromatics, thereby making it suitable as a high-octane gasoline blendstock. As the reformers reach capacity, coupled with the limited growth in the demand of aromatics, it is desirable to convert heavy naphtha, particularly heavy virgin naphtha (HVN), to large volume, higher value products.

Furthermore, global transportation fuels outlook suggests that the long-term demand for automotive gas (e.g., gasoline) will decrease, while the demand for high octane is expected to grow with the increasing use of high-compression engines. In addition, global fast growing demands for distillate (e.g., jet, diesel) favors the conversion of heavy naphtha (low-octane gasoline) to distillate range liquids. For example, research octane number ("RON") and motor octane number ("MON") for cyclohexane are 83.0 and 77.2, respectively, and RON and MON for n-heptane are zero. Therefore it is desirable to convert heavy naphtha to higher octane gasoline and/or distillate range liquids.

There is a need for improved methods of forming high octane gasoline and distillates from hydrocarbon streams (e.g., NGL and naphtha streams).

SUMMARY

In an embodiment, a process for converting a hydrocarbon feed includes introducing a hydrocarbon feed comprising a $C_2$-$C_{50}$ acyclic alkane and a $C_3$-$C_{50}$ cyclic alkane to a catalyst composition in a reactor. The process further includes converting the hydrocarbon feed in the reactor under reactor conditions to a product mixture comprising at least one of a $C_6$-$C_9$ aromatic product or a $C_{12+}$ distillate product.

In another embodiment, a process for converting a hydrocarbon feed includes introducing a hydrocarbon feed comprising a $C_2$-$C_{50}$ acyclic alkane and a $C_3$-$C_{50}$ cyclic alkane to a catalyst composition in a reactor, the catalyst composition comprising an acid. The process further includes converting the hydrocarbon feed in the reactor under reactor conditions to form a product mixture comprising at least one of a $C_6$-$C_9$ aromatic product or a $C_{12+}$ distillate product, wherein the reactor conditions include one or more of: a reactor temperature of 300° C. or lower, a reactor pressure of from 3.4 MPa gauge to 13.8 MPa gauge, or a liquid hourly space velocity (LHSV) of from about 0.01 $h^{-1}$ to about 200 $h^{-1}$.

In some embodiments, a process for converting a hydrocarbon feed includes introducing a hydrocarbon feed comprising one or more of a $C_6$-$C_{12}$ hydrocarbon to a catalyst composition in a reactor, the catalyst composition having a Si/Al molar ratio of 0.001 to 200, and a total surface area of from 100 $m^2/g$ to 800 $m^2/g$. The process further includes converting the hydrocarbon feed in the reactor under reactor conditions to form a product mixture comprising at least one of a $C_6$-$C_9$ aromatic product or a $C_{12+}$ distillate product, wherein the reactor conditions include one or more of: a reactor temperature of from 150° C. to 300° C., a reactor pressure of from 3.4 MPa gauge to 6.9 MPa gauge, or a liquid hourly space velocity (LHSV) of from about 0.01 $h^{-1}$ to about 200 $h^{-1}$.

DETAILED DESCRIPTION

The present disclosure provides processes to upgrade hydrocarbon feeds. Herein, this disclosure includes low temperature, liquid phase conversion of hydrocarbons (such as heavy naphtha, including paraffins and/or naphthene-rich heavy virgin naphtha, such as a $C_3$-$C_{50}$ cyclic alkane and/or a $C_2$-$C_{50}$ acyclic alkane (e.g., linear and or branched acyclic alkanes)) to high octane gasoline and/or distillate products over an acid catalyst in a single step without significant formation of light hydrocarbons (e.g., $C_1$-$C_4$ hydrocarbons). For example, it has been discovered that both aromatic products (such as $C_6$-$C_9$ aromatic products) and distillate products (such as $C_{12+}$ distillate products) can be formed using zeolite such as ZSM-5 as the acid catalyst. Additionally, it has been discovered that formation of aromatic products (such as $C_6$-$C_9$ aromatic products) can be substantially reduced (or eliminated), while distillate products (such as $C_{12+}$ distillates products) were formed, when using the MWW family of zeolite such as MCM-49 as the acid catalyst. Without being bound by theory, it is believed that the differing outcomes for formation of $C_6$-$C_9$ aromatic products between the ZSM-5 and MCM-49 zeolites are due to the arrangement of the 10-member ring channel of each zeolite. That is, the 10-member ring channel of ZSM-5 may be arranged in such a way as to allow formation of $C_6$-$C_9$ aromatic products (e.g., xylenes), whereas the 10-member ring channel of MCM-49 may be arranged such that $C_6$-$C_9$ aromatic products are inaccessible and most of the chemistry occurs in the surface pockets.

For purposes of this disclosure, and unless otherwise indicated, a "composition" includes components of the composition and/or reaction products of two or more components of the composition.

For purposes of this disclosure, and unless otherwise indicated, all numbers indicating quantities in this disclosure are to be understood as being modified by the term "about" in all instances. It should also be understood that the numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

For purposes of this disclosure, and unless otherwise indicated, the article "a" or "an" shall refer to "at least one" unless specified to the contrary or the context clearly indicates otherwise. Thus, embodiments comprising "an alkane" include embodiments comprising one, two, or more alkanes, unless specified to the contrary or the context clearly indicates only one alkane is included.

For purposes of this disclosure, and unless otherwise indicated, the nomenclature of elements is pursuant to the version of Periodic Table of Elements as described in CHEMICAL AND ENGINEERING NEWS, 63(5), pg. 27 (1985). Abbreviations for atoms are as given in the periodic table (Si=silicon, for example).

As used herein, and unless otherwise specified, the term "$C_n$" refers to hydrocarbon(s) having n carbon atom(s) per molecule, wherein n is a positive integer. For purposes of this disclosure, and unless otherwise indicated, the term "hydrocarbon" refers to a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different values of n. Additionally, the hydrocarbon compound may contain, for example, heteroatoms such as sulphur, oxygen, nitrogen, or any combination thereof.

For purposes of this disclosure, and unless otherwise indicated, the term "acyclic alkanes" includes linear and branched acyclic alkanes.

For purposes of this disclosure, and unless otherwise indicated, the term "acyclic alkenes" includes linear and branched acyclic alkenes.

For purposes of this disclosure, and unless otherwise indicated, the term "aryl," "aryl group," "aromatic," and "aromatic group" refers to an aromatic ring and the substituted variants thereof, such as phenyl, 2-methyl-phenyl, xylyl, 4-bromo-xylyl.

For purposes of this disclosure, and unless otherwise indicated, the terms "alkyl group," "alkyl radical," "hydrocarbyl radical," "hydrocarbyl," and "hydrocarbyl group," if used herein, are used interchangeably. Likewise, the terms "group," "radical," and "substituent," if used herein, are also used interchangeably. For purposes of this disclosure, "hydrocarbyl radical" is defined to be $C_1$-$C_{200}$ radicals, that may be linear, branched, or cyclic, and when cyclic, aromatic or non-aromatic. Examples of such radicals can include methyl, ethyl, n-propyl, isopropyl, n-butyl, isobutyl, sec-butyl, tert-butyl, pentyl, iso-amyl, hexyl, octyl, cyclopropyl, cyclobutyl, cyclopentyl, cyclohexyl, cyclooctyl, and the like including their substituted analogues. The alkyl group may be straight chain, branched, or cyclic. The alkyl group may be saturated or unsaturated. In at least one embodiment, the alkyl group may include at least one aromatic group.

For purposes of this disclosure, and unless otherwise indicated, the term "aralkyl" means a univalent radical derived from an alkyl radical by replacing one or more hydrogen atoms by one or more aryl groups.

For purposes of this disclosure, and unless otherwise indicated, the term "alkaryl" refers to an aryl-substituted alkyl radical (e.g., propyl-phenyl), such as a radical in which an aryl group is substituted for a hydrogen atom of an alkyl group.

For purposes of this disclosure, and unless otherwise indicated, the term "ring atom" refers to an atom that is part of a cyclic ring structure. By this definition, a benzyl group has six ring atoms and tetrahydrofuran has 5 ring atoms.

For purposes of this disclosure, and unless otherwise indicated, the term "conversion" refers to the degree to which a given reactant in a particular reaction (e.g., addition, dehydrogenation, etc.) is converted to products. Thus 100% conversion of cyclohexane means complete consumption of cyclohexane, and 0% conversion of cyclohexane refers to no measurable reaction of cyclohexane.

The term "medium pore zeolite" refers to a zeolite having a plurality of pores that have a 10-membered ring.

Embodiments disclosed herein include a liquid phase, low temperature conversion of a hydrocarbon feed (e.g., virgin naphtha) to $C_{3+}$ hydrocarbons such as high octane gasoline blend (e.g., $C_6$-$C_9$ aromatic products) and distillate products (e.g., $C_{12+}$ distillate products) using an MFI framework type zeolite (e.g., ZSM-5). Embodiments disclosed herein include a liquid phase, low temperature conversion of a hydrocarbon feed (e.g., virgin naphtha) to $C_{3+}$ hydrocarbons distillates (e.g., $C_{12+}$ distillates) using an MWW framework type zeolite (e.g., MCM-49).

Certain oils, e.g., unconventional oils (such as Permian Basin crudes), include a wide variety of liquid sources including oil sands, extra heavy oil, gas to liquids and other liquids. Unconventional oils, such as Permian Basin crude have been shown to contain large fractions of naphthenes in the naphtha range. Given the long-term outlook for transportation fuels, converting these molecules to heavier products such as distillate and aromatics is desirable.

Naphthenes, also known as cycloalkanes and/or cycloparaffins, have the same chemical formula as olefins, $C_nH_{2n}$. Without being bound by theory, it is believed that olefins can be alkylated with paraffins with an acid catalyst via a carbenium ion pathway.

The inventors envisioned that creation of a carbenium ion from a cycloalkane (via an acid-catalyzed pathway) would allow for a coupling of a paraffin to the cycloalkane in a mechanism similar to alkylation. As a non-limiting example, this concept is shown in an Example Scheme 1 and Example Scheme 2 below using cyclohexane (101) and n-heptane (104) as example feeds.

Example Scheme 1

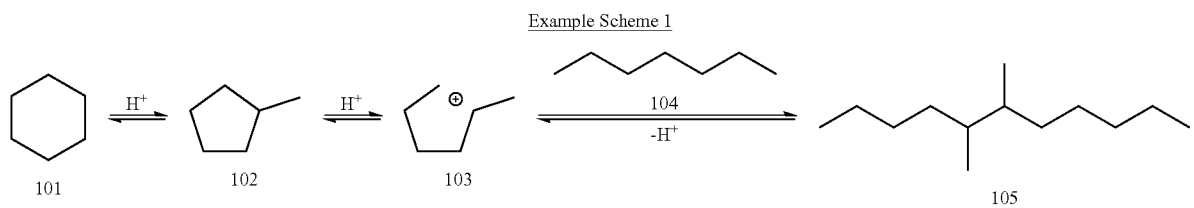

As discussed below, when the reaction is performed in the liquid phase using a zeolite catalyst, heavier products (e.g., $C_{12+}$) consistent with the chemistry discussed above are observed. Surprisingly, significant amounts of $C_8$ and $C_9$ aromatic products can also be formed. The $C_6$-$C_9$ aromatic products can be used as a high-octane blend and the $C_{12+}$ distillate products are in the distillate range. Therefore, the chemistry disclosed herein provides a method to convert low-quality naphtha to high octane gasoline and distillate in a simple process, an example of which is shown in the non-limiting Example Scheme 2. Although the schemes show a $C_{13}$ product as a non-limiting example, other products (e.g., $C_{12}$ products) can be obtained.

Example Scheme 2

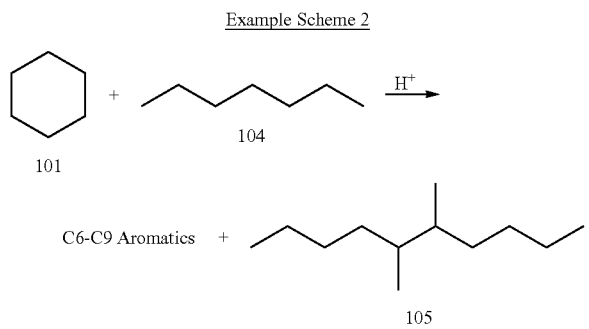

Herein, this disclosure includes a low temperature, liquid phase conversion of hydrocarbons (such as heavy naphtha, including paraffins and/or naphthene-rich heavy virgin naphtha, such as a $C_3$-$C_{50}$ cyclic and/or a $C_2$-$C_{50}$ acyclic alkanes (e.g., linear and or branched acyclic alkanes)) to a high octane gasoline product and/or a distillate product over an acid catalyst in a single step without significant formation of light hydrocarbons (e.g., $C_1$-$C_4$ hydrocarbons).

Processes for Converting Hydrocarbon Feeds

The present disclosure provides processes for converting (e.g., upgrading) a hydrocarbon feed (e.g., heavy naphtha) that includes introducing a hydrocarbon feed to a catalyst composition in a reactor, and converting the hydrocarbon feed in the reactor under reactor conditions to a product mixture comprising a $C_{3+}$ hydrocarbon product (such as at least one of $C_6$-$C_9$ aromatic products or $C_{12+}$ distillate products).

The hydrocarbon feed to be converted may include, in whole or in part, one or more of a $C_3$-$C_{50}$ cyclic alkane; a $C_2$-$C_{50}$ acyclic alkane (e.g., linear and or branched acyclic alkanes); a liquefied petroleum gas (LPG); NGL; a hydrocarbon feed having boiling point in the range of from about 70° C. to about 185° C. (e.g., a naphtha stream); heavy naphtha (including paraffins and/or naphthene-rich heavy virgin naphtha); heavy virgin naphtha; naphthenes; cat naphtha; coker naphtha; light paraffins obtained from Fischer-Tropsch synthesis; or a $C_6$-$C_{12}$ hydrocarbon (e.g., cyclohexane and n-heptane). The hydrocarbon feed to be converted may also include a gas oil (e.g., light, medium, or heavy gas oil) having an initial boiling point above 200° C., a 50% point of at least 260° C. and an end point of at least 350° C. The feed may also include vacuum gas oils, thermal oils, residual oils, cycle stocks, whole top crudes, tar sand oils, shale oils, synthetic fuels, heavy hydrocarbon fractions derived from the destructive hydrogenation of coal, tar, pitches, asphalts, hydrotreated feedstocks derived from any of the foregoing.

Heavy naphtha includes both paraffins and naphthenes (e.g., derived from coal, shale, or petroleum). For example, a naphtha may include from about 15 wt % to about 30 wt % paraffins, from about 5 wt % to about 20 wt % cycloparaffins, from about 10 wt % to about 30 wt % olefins, from about 1 wt % to about 10 wt % cycloolefins, and from about 10 wt % to about 40 wt % aromatics. Heavy naphtha can be converted to aromatics and distillates using the methods described herein. The heavy naphtha feed can be processed "as-is", or optionally separated into paraffin and naphthene fractions, or further fractionated to individual carbon number. The naphtha feed may include one or more of n-hexane, n-heptane, cyclopentane, cyclohexane, methylcyclohexane, methylcyclopentane, benzene, toluene, xylenes, or a mixture thereof. In some embodiments, processes of the present disclosure include the conversion of a $C_2$-$C_{50}$ acyclic alkanes and/or a $C_3$-$C_{50}$ cyclic alkane in a heavy naphtha range (including paraffins and/or naphthenes), to form a $C_{3+}$ hydrocarbon product (e.g., $C_{12+}$ distillate products and $C_6$-$C_9$ aromatic products).

Furthermore, the feed composition can be controlled by introducing, injecting, feeding, co-feeding, a defined amount of defined hydrocarbon starting materials, by controlling the ratio of the starting material. Accordingly, the average molecular weight of the products can be controlled subsequently. For instance, larger molecular weight range products can be produced when less acyclic starting material (e.g., linear acyclic paraffins) is introduced to the feed.

Alternatively, smaller molecular weight range products (e.g., shorter range diesel) can be produced when more linear acyclic starting material is added to the feed. For example, linear acyclic starting material, such as linear acyclic paraffins, can be combined with one or more cyclic and/or acyclic alkane(s) either before, or after, alternatively before and after, the introduction of one or more cyclic alkane(s) and acyclic alkane(s) into the reactor.

A process for converting a hydrocarbon feed can involve contacting a $C_2$-$C_{50}$ acyclic alkane feed (such as a $C_5$-$C_{25}$ acyclic alkane feed, such as a $C_6$-$C_9$ acyclic alkane feed) and/or a $C_3$-$C_{50}$ cyclic alkane feed (such as a $C_5$-$C_{25}$ acyclic alkane feed, such as a $C_6$-$C_9$ acyclic alkane feed) with a catalyst system including a solid acid, such as a ZSM-5 zeolite and/or a MCM-49 zeolite.

In a conversion process, a feed including about 2 wt % or more of a $C_2$-$C_{50}$ acyclic alkane and/or a $C_3$-$C_{50}$ cyclic alkane can be contacted with a catalyst suitable for a conversion process, with or without the presence of a solvent, and the hydrocarbons including a $C_2$-$C_{50}$ acyclic alkane and/or a $C_3$-$C_{50}$ cyclic alkane of the feed can be used directly as solvent.

Optionally one or more solvent(s) can be used for one or more processes of the present disclosure. The solvent may be a saturated hydrocarbon or an aromatic solvent such as heavy paraffins or aromatics with $C_{20+}$; sulfolane; glycols; glyme; or a mixture thereof. Contacting the catalyst with a feed comprising a $C_2$-$C_{50}$ acyclic alkane and/or a $C_3$-$C_{50}$ cyclic alkane may be carried out in an atmosphere inert under the process conditions, such as in nitrogen, argon, or a mixture thereof. Naphtha, including both paraffins and naphthenes, may include various ranges of cyclic and acyclic alkanes. Hence, controlling a co-feed molar ratio of cyclic alkanes to acyclic alkanes starting materials provides control of the molecular weight of the $C_{3+}$ hydrocarbon products, such as $C_5$-$C_{50}$ hydrocarbon products (such as $C_6$-$C_9$ aromatic products and $C_{12+}$ distillate products). Examples of $C_2$-$C_{50}$ acyclic alkanes can be ethane, propane, butane, pentane, hexane, heptane, octane, nonane, decane, undecane, dodecane, or a combination thereof. Examples of $C_3$-$C_{50}$ cyclic alkanes can be cyclopropane, cyclobutane, cyclopentane, cyclohexane, cycloheptane, cyclooctane, an isomer thereof, or a combination thereof.

In at least one embodiment, a molar ratio of one or more acyclic alkanes to cyclic alkanes can be from about 1:1000 to about 1000:1, such as from about 1:700 to about 700:1, such as from about 1:500 to about 500:1, such as from about 1:250 to about 250:1, such as from about 1:100 to about 100:1, such as from about 1:50 to about 50:1, such as from about 1:10 to about 10:1, such as from about 1:5 to about 5:1, such as from about 1:5 to about 1:2 or about 5:1 to about 2:1.

In at least one embodiment, a conversion process is performed at a temperature of about 400° C. or less, such as from about 100° C. to about 350° C., such as from about 150° C. to about 300° C. (e.g., about 200° C., about 225° C., about 250° C., about 260° C., or about 275° C.), and/or a pressure greater than 0.1 MPa gauge, such as from about 0.1 MPa gauge to about 50 MPa gauge, such as about 0.1 MPa gauge to about 20 MPa gauge, such as about 0.1 MPa gauge to about 15 MPa gauge, such as about 3.4 MPa to about 15 MP gauge, such as about 3.4 MPa gauge to about 13.8 MPa gauge, such as about 3.4 MPa gauge to about 6.9 MPa gauge, such as about 6.5 MPa gauge, and/or for a residence time of from about 1 min to about 20 h, such as from about 5 min to about 4 h, such as from about 10 min to about 3 h.

In some embodiments, a conversion process is performed where the feed is introduced into the reactor at a rate to achieve a liquid hourly space velocity (LHSV, volume of feed per unit volume of catalyst per hour) of from about 0.01 $h^{-1}$ to about 200 $h^{-1}$, such as from about 0.05 $h^{-1}$ to about 50 $h^{-1}$, such as about 0.1 $h^{-1}$ to about 10 $h^{-1}$.

A conversion process of the present disclosure may be carried out by mixing a solution of a $C_2$-$C_{50}$ acyclic alkane and/or a $C_3$-$C_{50}$ cyclic alkane and the catalyst composition(s) to form a mixture, cooling the mixture, and allowing the mixture to increase in temperature.

In at least one embodiment, conversion is performed at a temperature of about 250° C., and/or at a pressure of about 6.55 MPa gauge. In at least one embodiment, conversion is performed at a temperature of about 260° C., and/or at a pressure of about 6.55 MPa gauge.

In at least one embodiment, a process for the production of a $C_{3+}$ hydrocarbon product, such as a $C_5$-$C_{50}$ hydrocarbon product, such as a $C_6$-$C_9$ aromatic product and/or a $C_{12+}$ distillate product includes introducing a hydrocarbon feed comprising a $C_2$-$C_{50}$ acyclic alkane and/or a $C_3$-$C_{50}$ cyclic alkane to a catalyst composition in a reactor; and converting the hydrocarbon feed in the reactor under reactor conditions to form a product mixture comprising at least one $C_{3+}$ hydrocarbon product, such as at least one of a $C_5$-$C_{50}$ hydrocarbon product, such as at least one of a $C_6$-$C_9$ aromatic product and/or a $C_{12+}$ distillate product. In some embodiments, the $C_{3+}$ hydrocarbon product can be recovered and analyzed by GC.

In some embodiments, an amount of $C_3$-$C_{50}$ cyclic alkane converted to a product mixture can be greater than about 1%, such as from about 5 wt % to about 90 wt %, such as from about 20 wt % to about 75 wt %, such as about 25 wt % to about 70 wt %, based on the amount of $C_3$-$C_{50}$ cyclic alkane in the hydrocarbon feed.

In some embodiments, an amount of $C_3$-$C_{50}$ acyclic alkane converted to a product mixture can be greater than about 1%, such as from about 5 wt % to about 90 wt %, such as from about 20 wt % to about 75 wt %, such as about 25 wt % to about 70 wt %, based on the amount of $C_3$-$C_{50}$ cyclic alkane in the hydrocarbon feed.

Catalyst Compositions

In some embodiments, catalyst compositions of the present disclosure may include an acid other than zeolite or zeo-type.

In at least one embodiment, catalyst compositions of the present disclosure may include a solid acid, e.g., a molecular sieve. Examples of molecular sieves include medium pore zeolites identified by the International Zeolite Association (IZA) as having the MFI framework type (e.g., ZSM-5 zeolite) and the MWW framework type (e.g., MCM-49). Both ZSM-5 and MCM-49 are porous zeolites having 10-member ring channels.

MCM catalysts can be purchased or made according to U.S. Pat. No. 5,236,575; Lawton, Stephen L. et al., "Zeolite MCM-49: A Three-Dimensional MCM-22 Analog Synthesized by in situ Crystallization", Journal of Physical Chemistry, 1996, 100(9), 3788-3798.

ZSM catalysts can be prepared according to U.S. Pat. Nos. 3,702,886, 4,797,267, or 5,783,321.

In some embodiments, the ZSM-5 and/or MCM-49 (and/or other MFI/MWW framework type zeolites) can have a silicon to aluminum molar ratio (Si/Al molar ratio) of from about 5:1 to about 100:1, such as from about 10:1 to about 40:1. In some embodiments, the Si/Al molar ratio is from about 0.001 to about 500, such as from about 0.002 to about 200, such as from about 0.003 to about 40, such as from about 0.1 to about 35, such as from about 1 to about 30, such as from about 5 to about 25, such as from about 7.5 to about 20, such as from about 5 to about 12.

In some embodiments, the zeolite can have a total surface area of from about 100 $m^2/g$ to about 800 $m^2/g$, such as from about 200 $m^2/g$ to about 650 $m^2/g$, such as from about 250 $m^2/g$ to about 600 $m^2/g$, as measured by BET surface adsorption. In some embodiments, the zeolite can have a total pore volume of about 0.1 mL/g to about 0.8 mL/g, such as from about 0.15 mL/g to about 0.7 mL/g, such as from about 0.2 mL/g to about 0.6 mL/g, as measured by BET surface adsorption.

In some embodiments, the zeolite can have a hydrocarbon sorption capacity (e.g., n-hexane sorption) at about 75 torr, about 90° C., of about 40 mg/g to about 150 mg/g, such as from about 50 mg/g to about 150 mg/g, such as from about 60 mg/g to about 150 mg/g alternatively from about 70 mg/g to about 150 mg/g, as measured by Thermal Gravimetric Analysis (TGA).

As used herein, "mesopore volume" is the accumulated volume in the pore size range of from about 2 nm to about 50 nm of the mesopore zeolite. The total mesopore volume can be of from about 0.1 mL/g to about 0.8 mL/g, such as from about 0.15 mL/g to about 0.75 mL/g, such as from about 0.2 mL/g to about 0.7 mL/g, such as about 0.32 mL/g to about 0.36 mL/g, as measured by BET surface adsorption.

In some embodiments, a catalyst composition loading % (based on the concentration of the alkanes and cycloalkanes for the conversion reaction) can be from about 0.01 mol % to about 50 mol %, such as from about 0.1 mol % to about 25 mol %, such as from about 0.2 mol % to about 10 mol %, such as from about 0.5 mol % to about 5 mol %, for example about 0.2 mol %.

The catalyst system can be neat or bounded with a binder. The catalyst composition of this disclosure may comprise a solid acid of this disclosure, e.g., comprising ≥about 85 wt %, or ≥about 90 wt %, or ≥about 95 wt %, or ≥about 98 wt %, or even ≥about 99 wt % of the solid acid, based on the total weight of the catalyst composition. Such catalyst composition may be considered as a "neat catalyst" in that it comprises minor amount of binder or support material in its composition, if any at all.

Optional Diluent Materials for the Catalyst Compositions

In some embodiments, the catalyst composition may include a diluent material (e.g., an inert diluent material). The catalyst composition of this disclosure can comprise a diluent at any suitable quantity, e.g., ≥about 20 wt %, ≥about 30, ≥about 40, ≥about 50 wt %, ≥about 60 wt %, ≥about 70 wt %, ≥about 80 wt %, ≥about 90 wt %, or even ≥about 95 wt %, based on the total weight of the catalyst composition. In the catalyst compositions, the zeolite can be disposed on the internal or external surfaces of the diluent material.

Diluent materials may include silicon carbide, quartz, and other inert materials such as silica, clays.

The diluent material can be dry, that is, free of absorbed water. Drying of the diluent material can be effected by heating or calcining at about 100° C. to about 1000° C., such as at least about 400° C. The calcined diluent material can then be contacted with at least one solid acid catalyst.

The diluent material can be slurried in a non-polar solvent and the resulting slurry can be contacted with a solution of a solid acid catalyst(s). In at least one embodiment, the slurry of the diluent material can be contacted with a solid acid catalyst for a period of time in the range of from about 0.5 h to about 24 h, such as from about 2 h to about 16 h, such as from about 4 h to about 8 h.

The mixture of the zeolite and diluent material can be heated to a temperature of from about 0° C. to about 70° C., such as from about 23° C. to about 60° C., such as about room temperature. Contact times may range from about 0.5 h to about 24 h, such as from about 2 h to about 16 h, such as from about 4 h to about 8 h.

Optional Binder or Support Materials for the Catalyst Compositions

In some embodiments, the catalyst composition may include a support material (e.g., an inert support material, also known as binder). The catalyst composition of this disclosure can include a catalyst support material (which may be called a carrier or a binder), at any suitable quantity, e.g., ≤about 20 wt %, ≤about 30 wt %, ≤about 40 wt %, ≤about 50 wt %, ≤about 60 wt %, ≤about 70 wt %, ≤about 80 wt %, ≤about 90 wt %, or even ≤about 95 wt %, based on the total weight of the catalyst composition. In catalyst compositions that include a support, the zeolite can be disposed on the internal or external surfaces of the catalyst support material.

Catalyst support materials or binder may include porous materials that provide mechanical strength and a high surface area. Non-limiting examples of suitable support materials can include oxides (e.g. silica, alumina, titania, zirconia, and mixtures thereof), carbides, nitrides, treated oxides (e.g. sulphated), crystalline microporous materials, non-crystalline microporous materials, cationic clays or anionic clays (e.g. saponite, bentonite, kaoline, sepiolite, hydrotalcite), carbonaceous materials, or combinations and mixtures thereof.

The support material can be dry, that is, free of absorbed water. Drying of the support material can be effected by heating or calcining at a temperature from about 100° C. to about 1000° C., such as at least about 400° C. When the support material is silica, it can be heated to at least about 110° C., such as from about 110° C. to about 850° C., such as at about 600° C., for example; and/or for a time of from about 1 min to about 100 h, such as from about 12 h to about 72 h, such as from about 24 h to about 60 h. The calcined support material can have at least some reactive hydroxyl (OH) groups to produce supported catalyst systems of the present disclosure. The calcined support material can then be contacted with at least one solid acid catalyst.

The support material, having reactive surface groups, such as hydroxyl groups, can be slurried in a non-polar solvent and the resulting slurry can be contacted with a solution of a solid acid catalyst(s). In at least one embodiment, the slurry of the support material can be contacted with a solid acid catalyst for a period of time in the range of from about 0.5 h to about 24 h, such as from about 2 h to about 16 h, such as from about 4 h to about 8 h.

The mixture of the zeolite and the binder or support material can be heated to a temperature of from about 0° C. to about 700° C., such as from about 23° C. to about 600° C. Contact times may range from about 0.5 h to about 24 h, from about 2 h to about 16 h, or from about 4 h to about 8 h.

Products of the Conversion Process

The methods of this disclosure provide for various products that include a $C_{3+}$ hydrocarbon, such as a $C_3$-$C_{50}$ hydrocarbon, such as a $C_5$-$C_{50}$ hydrocarbon, such as a $C_6$-$C_9$ aromatic product or a $C_{12+}$ distillate product. Examples of products include propane, isobutane, n-butane, 2-methyl-butane, pentane, 2,3-dimethyl-butane, 2-methyl-pentane, 3-methyl-pentane, n-hexane, methyl-cyclopentane, 2,4-dimethyl-pentane, 2,2-dimethyl-pentane, cyclohexene, cyclohexane, n-heptane, other $C_7$ compounds, $C_8$ compounds (cyclic), $C_8$ compounds (aromatic), $C_9$ compounds (aromatic), $C_{10}$ compounds, $C_{12}$ compounds, and $C_{13+}$ compounds. In some embodiments, a product mixture includes at least one of a $C_6$-$C_9$ aromatic product(s) or a $C_{12+}$ distillate product(s).

In some embodiments, the product mixture can include a $C_6$-$C_9$ aromatic product content of from about 0.01 wt % to about 30 wt % (such as about 25 wt % or lower, such as from about 0.01 wt % to about 5 wt %), and/or a $C_{12+}$ distillate product content of from about 50 wt % to about 99 wt % (such as from about 60 wt % to about 98 wt %, such as from 70 wt % to about 90 wt %), based on a total weight of the product mixture.

Certain products of the conversion process described herein can be useful for diesel fuels and useful for a high-octane gasoline blend component with a RON greater than about 90, about 93, or about 95.

A. Diesel Fuels

Products of the present disclosure can be used as diesel fuels. The products can be formed from the conversion of a $C_2$-$C_{50}$ acyclic alkane and/or a $C_3$-$C_{50}$ cyclic alkane, the diesel fuels having one or more of improved low temperature properties, an improved cloud point, and a high cetane number. In at least one embodiment, a diesel fuel is a $C_5$-$C_{50}$ hydrocarbon, such as a $C_{12}$-$C_{25}$ hydrocarbon.

Cetane number is a measure of ignition quality of diesel fuels. Cetane number is highly dependent on the paraffinicity of molecular structures whether they be straight chain or alkyl attachments to rings. Distillate aromatic content, for example, is inversely proportional to cetane number while a high paraffinic content is directly proportional to a high cetane number. Generally, diesel engines operate well with a cetane number of from 48 to 50. Fuels with a lower cetane number have longer ignition delays, requiring more time for the fuel combustion process to be completed. Hence, higher speed diesel engines operate more effectively with higher cetane number fuels. A product of the present disclosure can be useful as a diesel fuel, as indicated by advantageous cetane numbers. For example, the product(s) formed by methods described herein can have a cetane number of about 30 or greater, such as about 40 or greater, such as about 45 or greater, such as about 48 or greater, such as about 50 or greater, such as about 60 or greater, such as about 70 or greater, such as about 80 or greater, such as about 90 or greater.

Under present conditions, petroleum refineries are finding it increasingly necessary to seek the most cost-effective ways of improving the quality of diesel fuel products. The methods described herein can meet this need.

B. High Octane Gasoline

The $C_6$-$C_9$ aromatic products can be useful as a high-octane gasoline blend component with a RON greater than about 90, about 93, or about 95. The octane number for typical aromatics is as follows: toluene (MON=100.3), ethylbenzene (MON=97.9; RON=100.8), o-xylene (MON=100), m-xylene (MON=102.8; RON=104), n-propylbenzene (MON=98.7; RON=101.5).

EXAMPLES

Calculations

To evaluate whether the carbenium ion pathway is thermodynamically allowed, the free energy of the reaction (ΔG) is calculated using HSC Chemistry (version 5.1) software. 3-methyldodecane (106) is chosen to represent the products of the coupling reaction as shown in Example Scheme 3 because its thermodynamic data is available.

Example Scheme 3

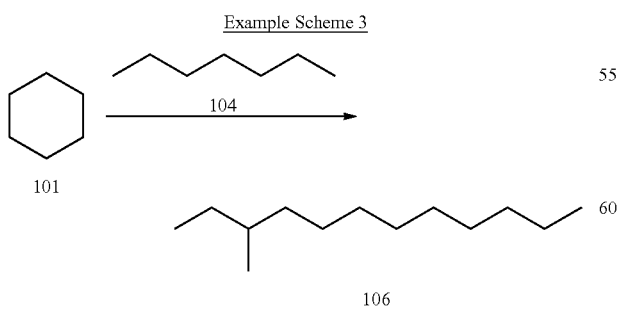

The gas-phase reaction is thermodynamically un-favored at both 0° C. and 250° C.: ΔG=4.1 kcal/mol at 0° C.; and 8.4 kcal/mol at 250° C. However, when the calculation is run in the liquid phase, the free energy is much more favorable at both 0° C. and 250° C.: ΔG=1.2 kcal/mol at 0° C.; and 1.8 kcal/mol at 250° C. Therefore the reaction is thermodynamically possible in the liquid phase.

Determination of Products

The various types of hydrocarbons formed of the present disclosure can be determined using Gas Chromatography-mass spectrometry.

Gas Chromatography (GC): For the conversion process, the products were analyzed using a GC (Agilent 6890 Plus) with an FID detector and a HP-PONA column (50 m length×0.2 mm diameter×0.5 μm film thickness). The GC conditions were the following: Injector: 225° C.; 0.5 μL injection volume, 100/1 split ratio. Detector: 250° C. Oven: 35° C. (10 min), 2.5° C./min to 135° C., 10° C./min to 320° C. (6.5 min).

Reactants and reagents were purchased from Aldrich as anhydrous grade and used as received.

Part A. Preparation of the Solid Acid

Example A1: Preparation of ZSM-5. ZSM-5 Can be Prepared According to U.S. Pat. Nos. 3,702,886, 4,797,267, or 5,783,321

Example A2: Preparation of MCM-49. MCM-49 Can be Prepared According to U.S. Pat. No. 5,236,575

Part B. Processes for Converting Hydrocarbon Feeds

Example B1: Process for Converting Cyclohexane Using a ZSM-5 Catalyst Composition of this Disclosure The reaction was carried out using a down-flow, tubular, fixed-bed reactor equipped with two ISCO pumps and various gas feeds. Cyclohexane was delivered via an ISCO pump through a heated section before entering the reactor (0.5" O.D.×16.75"×0.028" (1.27 cm O.D.×42.5 cm×0.071 cm) wall stainless steel tube) packed with ZSM-5 catalyst (about 1.0 g) diluted with silicon carbide to a total volume of about 4 mL. A piece of 0.25" (0.635 cm) O.D. stainless steel thermal well was inserted at the bottom of the reactor tube for temperature measurement. The reactor pressure was controlled via a Mity-Mite back pressure regulator. The reactor effluent was heat-traced to an on-line GC for analysis and collected in knock-out pots (a heated pot followed by a chilled pot held at about 5° C.) for off-line analysis and total liquid products mass balance. The reactor was first purged with $N_2$ for about 12 hours or more at the desired reaction temperature before introducing the liquid feed. The heated zones, including the feed pre-heater, reactor effluent, and heated knock-out were maintained at the same temperature as the reactor. Typical reactor conditions include: a pressure of about 950 psig (about 6.5 MPa gauge) to ensure the reactor is liquid full and the reaction is occurring in the liquid phase, a temperature of about 250° C., a cyclohexane feed rate of about 1 mL/h.

Example B2: Process for Converting Cyclohexane/Heptane Using a ZSM-5 Catalyst Composition of this Disclosure The reaction was carried out using a down-flow, tubular, fixed-bed reactor equipped with two ISCO pumps and various gas feeds. Cyclohexane and n-heptane were delivered via an ISCO pump through a heated section before entering the reactor (0.5" O.D.×16.75"×0.028" (1.27 cm O.D.×42.5 cm×0.071 cm) wall stainless steel tube) packed with ZSM-5 catalyst (about 1.0 g) diluted with silicon carbide to a total volume of about 4 mL. A piece of 0.25" (0.635 cm) O.D. stainless steel thermal well was inserted at the bottom of the reactor tube for temperature measurement. The reactor pressure was controlled via a Mity-Mite back pressure regulator. The reactor effluent was heat-traced to an on-line GC for analysis and collected in knock-out pots (a heated pot followed by a chilled pot held at about 5° C.) for off-line analysis and total liquid products mass balance. The reactor was first purged with $N_2$ for about 12 hours at the desired reaction temperature before introducing the liquid feed. The heated zones, including the feed pre-heater, reactor effluent, and heated knock-out were maintained at the same temperature as the reactor. Typical reactor conditions include: a pressure of about 950 psig (about 6.5 MPa gauge) to ensure the reactor is liquid full and the reaction is occurring in the liquid phase, a temperature of about 250° C., a cyclohexane feed rate of about 1 mL/h, and a n-heptane feed rate of about 1 mL/h.

Example B3: Process for Converting Cyclohexane Using a MCM-49 Catalyst Composition of this Disclosure The reaction was carried out using a down-flow, tubular, fixed-bed reactor equipped with two ISCO pumps and various gas feeds. Cyclohexane was delivered via an ISCO pump through a heated section before entering the reactor (0.5" O.D.×16.75"×0.028" (1.27 cm O.D.×42.5 cm×0.071 cm) wall stainless steel tube) packed with MCM-49 catalyst (about 1.0 g) diluted with silicon carbide to a total volume of about 4 mL. A piece of 0.25" (0.635 cm) O.D. stainless steel thermal well was inserted at the bottom of the reactor tube for temperature measurement. The reactor pressure was controlled via a Mity-Mite back pressure regulator. The reactor effluent was heat-traced to an on-line GC for analysis and collected in knock-out pots (a heated pot followed by a chilled pot held at about 5° C.) for off-line analysis and total liquid products mass balance. The reactor was first purged with $N_2$ for about 12 hours at the desired reaction temperature before introducing the liquid feed. The heated zones, including the feed pre-heater, reactor effluent, and heated knock-out were maintained at the same temperature as the reactor. Typical reactor conditions include: a pressure of about 950 psig (about 6.5 MPa gauge) to ensure the reactor is liquid full and the reaction is occurring in the liquid phase, a temperature of about 250° C., a cyclohexane feed rate of about 1 mL/h.

Example B4: Process for Converting Cyclohexane/Heptane Using a MCM-49 Catalyst Composition of this Disclosure The reaction was carried out using a down-flow, tubular, fixed-bed reactor equipped with two ISCO pumps and various gas feeds. Cyclohexane and n-heptane were delivered via separate ISCO pumps connected via a T and mixed through a heated section before entering the reactor (0.5" O.D.×16.75"×0.028" (1.27 cm O.D.×42.5 cm×0.071 cm) wall stainless steel tube) packed with MCM-49 catalyst (about 1.0 g) diluted with silicon carbide to a total volume of about 4 mL. A piece of 0.25" (0.635 cm) O.D. stainless steel thermal well was inserted at the bottom of the reactor tube for temperature measurement. The reactor pressure was controlled via a Mity-Mite back pressure regulator. The reactor effluent was heat-traced to an on-line GC for analysis and collected in knock-out pots (a heated pot followed by a chilled pot held at about 5° C.) for off-line analysis and total liquid products mass balance. The reactor was first purged with $N_2$ for about 12 hours at the desired reaction temperature before introducing the liquid feed. The heated zones, including the feed pre-heater, reactor effluent, and heated knock-out were maintained at the same temperature as the reactor. Typical reactor conditions include: a pressure of about 950 psig (about 6.5 MPa gauge) to ensure the reactor is liquid full and the reaction occurs in the liquid phase, a temperature of about 250° C., a cyclohexane feed rate of about 1 mL/h, a n-heptane feed rate of about 1 mL/h.

Example B5: Process for Converting Cyclohexane/Heptane at 260° C. Using a MCM-49 Catalyst Composition of this Disclosure The reaction was carried out using a down-flow, tubular, fixed-bed reactor equipped with two ISCO pumps and various gas feeds. Cyclohexane and n-heptane were delivered via separate ISCO pumps connected via a T and mixed through a heated section before entering the reactor (0.5" O.D.×16.75"×0.028" (1.27 cm O.D.×42.5 cm×0.071 cm) wall stainless steel tube) packed with MCM-49 catalyst (about 1.0 g) diluted with silicon carbide to a total volume of about 4 mL. A piece of 0.25" (0.635 cm) O.D. stainless steel thermal well was inserted at the bottom of the reactor tube for temperature measurement. Reactor pressure was controlled via a Mity-Mite back pressure regulator. The reactor effluent was heat-traced to an on-line GC for analysis and collected in knock-out pots (a heated pot followed by a chilled pot held at about 5° C.) for off-line analysis and total liquid products mass balance. The reactor was first purged with $N_2$ for about 12 hours at the desired reaction temperature before introducing the liquid feed. The heated zones, including the feed pre-heater, reactor effluent, and heated knock-out were maintained at the same temperature as the reactor. Typical reactor conditions include: a pressure of about 950 psig (about 6.5 MPa gauge) to ensure the reactor is liquid full and the reaction is occurring in the liquid phase, a temperature of about 260° C., a cyclohexane feed rate of about 1 mL/h, a n-heptane feed rate of about 1 mL/h.

TABLE I

| Example No. | B1 | B2 | B3 | B4 | B5 |
|---|---|---|---|---|---|
| Catalyst | ZSM-5 | ZSM-5 | MCM-49 | MCM-49 | MCM-49 |
| Cyclohexane feed rate (mL/h) | 1.0 | 1.0 | 1.0 | 1.0 | 1.0 |
| n-Heptane feed rate (mL/h) | — | 1.0 | — | 1.0 | 1.0 |
| Reactor Temperature (° C.) | 250 | 250 | 250 | 250 | 260 |
| Reactor Pressure (MPa) | 6.5 | 6.5 | 6.5 | 6.5 | 6.5 |
| Product Composition (wt %) | | | | | |
| Propane | 0.21 | 0.69 | 0.04 | 0.10 | 0.02 |
| Isobutene | 0.05 | 0.45 | 0.04 | 0.15 | 0.06 |
| n-butane | 0.16 | 0.54 | 0.02 | 0.01 | 0.02 |

TABLE I-continued

| Example No. | B1 | B2 | B3 | B4 | B5 |
|---|---|---|---|---|---|
| butane, 2-Methyl- | 0.05 | 0.23 | 0.01 | 0.04 | 0.02 |
| Pentane | 0.08 | 0.38 | — | 0.01 | 0.01 |
| butane, 2,3-Dimethyl- | 0.01 | 0.01 | — | — | — |
| pentane, 2-Methyl- | 0.21 | 0.22 | 0.02 | 0.01 | 0.01 |
| pentane, 3-Methyl- | 0.09 | 0.07 | 0.01 | 0.01 | — |
| n-Hexane | 0.21 | 0.28 | 0.01 | 0.01 | 0.01 |
| cyclopentane, Methyl- | 6.25 | 1.74 | 5.90 | 2.86 | 0.98 |
| pentane, 2,4-Dimethyl- | 0.0 | 0.01 | — | 0.03 | 0.01 |
| pentane, 2,2-Dimethyl- | — | — | — | 0.01 | — |
| Cyclohexene | 0.02 | 0.02 | — | 0.01 | — |
| Cyclohexane | 26.11 | 12.18 | 83.72 | 41.29 | 22.51 |
| n-heptane | 0.33 | 12.64 | 0.24 | 39.53 | 23.28 |
| Other $C_7$ compounds | 0.33 | 3.14 | 0.06 | 0.78 | 0.35 |
| $C_8$ compounds (cyclic) | 0.59 | 1.46 | 0.03 | 0.04 | 0.02 |
| $C_8$ compounds (aromatic) | 1.94 | 4.54 | 0.01 | 0.01 | 0.01 |
| $C_9$ compounds (aromatic) | 4.47 | 10.67 | — | 0.01 | 0.02 |
| $C_{10}$ compounds | 8.26 | 14.19 | 0.61 | 0.76 | 0.34 |
| $C_{12}$ compounds | 12.34 | 13.41 | 3.22 | 2.68 | 2.06 |
| $C_{13+}$ compounds | 38.32 | 23.16 | 6.07 | 11.68 | 50.29 |
| ‡ Liquid products recovered (wt %) | — | 85.8 | 95.0 | 91.4 | 87.8 |
| Cyclohexane conversion (wt %) | 74 | 77 | 16 | 22 | 58 |
| n-Heptane conversion (wt %) | — | 73 | — | 16 | 50 |

‡ Liquid products recovered refers to $C_{5+}$ liquid hydrocarbons.

The data in Table I show that a significant amount of $C_6$-$C_9$ aromatic products are formed when a ZSM-5 catalyst is employed. However, aromatic products are substantially reduced when MCM-49 is used as a catalyst, with the distillate products range (e.g., $C_{12+}$) as the dominant products. The data show that an MFI framework type zeolite (e.g., ZSM-5) can be used for a liquid phase, low temperature conversion of a hydrocarbon feed (e.g., virgin naphtha) to $C_{3+}$ hydrocarbons such as high octane gasoline blend (e.g., $C_6$-$C_9$ aromatic products) and distillates products (e.g., $C_{12+}$ distillate products). The data additionally show that a MWW framework type zeolite (e.g., MCM-49) can be used for a liquid phase, low temperature conversion of a hydrocarbon feed (e.g., virgin naphtha) to $C_{3+}$ hydrocarbons distillates (e.g., $C_{12+}$ distillates).

The data also shows that temperature can have a significant effect on the conversion process. For example, at 260° C., the amount of $C_{13+}$ compounds increased (see Examples B4 and B5). Plus, the addition of n-heptane to the reaction shows observable differences in the amount of $C_8$ compounds (aromatic) produced by the addition of n-heptane for the ZSM-5 catalyzed reaction (see Examples B1 and B2). Moreover, the amount of $C_{13+}$ compounds produced by the addition of n-heptane for the MCM49 catalyzed reaction can be temperature and catalyst dependent (compare Examples B1-B5).

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

The phrases, unless otherwise specified, "consists essentially of" and "consisting essentially of" do not exclude the presence of other steps, elements, or materials, whether or not, specifically mentioned in this specification, so long as such steps, elements, or materials, do not affect the basic and novel characteristics of the present disclosure, additionally, they do not exclude impurities and variances normally associated with the elements and materials used.

All documents described herein are incorporated by reference herein, including any priority documents and/or testing procedures to the extent they are not inconsistent with this text. As is apparent from the foregoing general description and the specific embodiments, while forms of this disclosure have been illustrated and described, various modifications can be made without departing from the spirit and scope of this disclosure. Accordingly, it is not intended that this disclosure be limited thereby. Likewise, the term "comprising" is considered synonymous with the term "including" for purposes of United States law. Likewise whenever a composition, an element or a group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

While this disclosure has been described with respect to a number of embodiments and examples, those skilled in the art, having benefit of this disclosure, will appreciate that other embodiments can be devised which do not depart from the scope and spirit of this disclosure.

What is claimed is:

1. A process for converting a hydrocarbon feed, comprising:
   introducing a hydrocarbon feed comprising a $C_2$-$C_{50}$ acyclic alkane and a $C_3$-$C_{50}$ cyclic alkane to a catalyst composition in a reactor in a liquid phase; and
   converting the hydrocarbon feed in the reactor in the liquid phase under reactor conditions to a product mixture comprising at least one of a $C_6$-$C_9$ aromatic product or a $C_{12+}$ distillate product;
   wherein the catalyst composition consists essentially of an acid.

2. The process of claim 1, wherein the hydrocarbon feed comprises a $C_6$-$C_{12}$ hydrocarbon.

3. The process of claim 1, wherein the hydrocarbon feed comprises a mixture of hydrocarbons having a boiling point from 70° C. to 185° C.

4. The process of claim 1, wherein the hydrocarbon feed comprises one or more of n-hexane, n-heptane, cyclopentane, cyclohexane, methylcyclohexane, methyl-cyclopentane, benzene, toluene, xylenes, or a mixture thereof.

5. The process of claim 1, wherein the $C_2$-$C_{50}$ acyclic alkane is selected from the group consisting of ethane, propane, butane, pentane, hexane, heptane, octane, nonane, decane, undecane, dodecane, and a combination thereof.

6. The process of claim 1, wherein the $C_3$-$C_{50}$ cyclic alkane s selected from the group consisting of cyclopropane, cyclobutane, cyclopentane, cyclohexane, cycloheptane, cyclooctane, isomers, and a combination thereof.

7. The process of claim 1, wherein the $C_3$-$C_{50}$ cyclic alkane is cyclohexane and the $C_2$-$C_{50}$ acyclic alkane is heptane.

8. The process of claim 1, wherein a molar ratio of acyclic alkane to cyclic alkane is from 1:5 to 5:1.

9. The process of claim 8, wherein the molar ratio of acyclic alkane to cyclic alkane is from 1:5 to 1:2.

10. The process of claim 1, wherein the reactor conditions include one or more of a reactor temperature of 400° C. or lower, a reactor pressure of from 3.4 MPa gauge to 13.8 MPa gauge, or a liquid hourly space velocity (LHSV) of from about 0.01 $h^{-1}$ to about 200 $h^{-1}$.

11. The process of claim 10, wherein the reactor conditions include one or more of the reactor temperature is from 150° C. to 300° C., the reactor pressure is from 3.4 MPa gauge to 6.9 MPa gauge, or the LHSV is from about 0.1$h^{-1}$ to about 10 $h^{-1}$.

12. The process of claim 1, wherein the catalyst composition consists essentially of a zeolite having a Si/Al molar ratio of 0.001 to 500, a ring size of at least a 10-membered ring.

13. The process of claim 1, wherein the product mixture includes a $C_6$-$C_9$ aromatic product content of from 0.01 wt % to 30 wt %, and a $C_{12+}$ distillate product content of from 50 wt % to 99 wt %, based on a total weight of the product mixture.

14. The process of claim 13, wherein the $C_6$-$C_9$ aromatic product content is from 0.01 wt % to 5 wt % based on the total weight of the product mixture, and the $C_{12+}$ distillate product content is 60 wt % or higher based on the total weight of the product mixture.

15. The process of claim 1, wherein an amount of $C_3$-$C_{50}$ cyclic alkane converted to the product mixture is from 5 wt % to 90 wt %, based on the amount of $C_3$-$C_{50}$ cyclic alkane in the hydrocarbon feed.

16. The process of claim 1, wherein an amount of $C_2$-$C_{50}$ acyclic alkane converted to the product mixture is from 5 wt % to 90 wt %, based on the amount of $C_2$-$C_{50}$ acyclic alkane in the hydrocarbon feed.

17. The process of claim 1, wherein the catalyst composition consists essentially of a zeolite having a Si/Al molar ratio of 0.001 to 200.

18. The process of claim 13, wherein the product mixture includes a $C_{12+}$ distillate product content of from 70 wt % to 90 wt %, and a $C_6$-$C_9$ aromatic product content of from 0.01 wt % to 30 wt %, based on a total weight of the product mixture.

19. The process of claim 13, wherein the $C_{12+}$ distillate product content is from 50 wt % to 90 wt % based on a total weight of the product mixture.

20. The process of claim 13, wherein the $C_6$-$C_9$ aromatic product content is 25 wt % or lower based on a total weight of the product mixture.

21. The process of any claim 1, wherein the catalyst composition includes a diluent, a support material, or a combination thereof.

22. The process of claim 12, wherein the zeolite has a total surface area of from 100 $m^2/g$ to 800 $m^2/g$.

23. A process for converting a hydrocarbon feed, comprising:

introducing a hydrocarbon feed comprising a $C_2$-$C_{50}$ acyclic alkane and a $C_3$-$C_{50}$ cyclic alkane to a catalyst composition in a reactor in a liquid phase, the catalyst composition comprising an acid; and converting the hydrocarbon feed in the reactor in the liquid phase, under reactor conditions to form a product mixture comprising at least one of a $C_6$-$C_9$ aromatic product or a $C_{12+}$ distillate product, wherein the reactor conditions include one or more of:

a reactor temperature of 300° C. or lower, a reactor pressure of from 3.4 MPa gauge to 13.8 MPa gauge, or a liquid hourly space velocity (LHSV) of from about 0.01 $h^{-1}$ to about 200 $h^{-1}$.

24. A process for converting a hydrocarbon feed, comprising:

introducing a hydrocarbon feed comprising one or more of a $C_6$-$C_{12}$ hydrocarbon to a catalyst composition in a reactor in a liquid phase, the catalyst composition having a Si/Al molar ratio of 0.001 to 200, and a total surface area of from 100 $m^2/g$ to 800 $m^2/g$; and converting the hydrocarbon feed in the reactor in the liquid phase, under reactor conditions to form a product mixture comprising at least one of a $C_6$-$C_9$ aromatic product or a $C_{12+}$ distillate product, wherein the reactor conditions include one or more of:

a reactor temperature of from 150° C. to 300° C., a reactor pressure of from 3.4 MPa gauge to 6.9 MPa gauge, or a liquid hourly space velocity (LHSV) of from about 0.01 $h^{-1}$ to about 200 $h^{-1}$.

* * * * *